US009687437B2

(12) United States Patent
Garrison et al.

(10) Patent No.: US 9,687,437 B2
(45) Date of Patent: *Jun. 27, 2017

(54) METHODS AND COMPOSITIONS FOR PREVENTING OR REDUCING FRIZZY APPEARANCE OF HAIR

(71) Applicant: Avon Products, Inc., Suffern, NY (US)

(72) Inventors: Mark S. Garrison, Suffern, NY (US); Freda E. Robinson, Nyack, NY (US); Giovana A. Sandstrom, Saddle Brook, NY (US); Kenneth A. Buckridge, North Reading, MA (US); Sen Yang, Highland, NY (US); Xiaochun Luo, New City, NY (US)

(73) Assignee: Avon Products, Inc, Rye, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/560,602

(22) Filed: Dec. 4, 2014

(65) Prior Publication Data
US 2015/0093422 A1  Apr. 2, 2015

Related U.S. Application Data

(63) Continuation of application No. 12/912,859, filed on Oct. 27, 2010, now Pat. No. 8,932,569.

(60) Provisional application No. 61/258,651, filed on Nov. 6, 2009.

(51) Int. Cl.
A61Q 5/06 (2006.01)
A61K 8/898 (2006.01)
A61K 8/25 (2006.01)
A61K 8/26 (2006.01)
A61K 8/895 (2006.01)
A61K 8/91 (2006.01)
A61K 8/34 (2006.01)
A61K 8/37 (2006.01)
A61K 8/41 (2006.01)
A61K 8/81 (2006.01)
A61K 8/86 (2006.01)
A61K 8/891 (2006.01)
A61K 8/897 (2006.01)
A61K 8/58 (2006.01)
A61K 8/02 (2006.01)

(52) U.S. Cl.
CPC ............... A61K 8/898 (2013.01); A61K 8/25 (2013.01); A61K 8/26 (2013.01); A61K 8/34 (2013.01); A61K 8/37 (2013.01); A61K 8/416 (2013.01); A61K 8/585 (2013.01); A61K 8/8152 (2013.01); A61K 8/86 (2013.01); A61K 8/891 (2013.01); A61K 8/895 (2013.01); A61K 8/897 (2013.01); A61K 8/91 (2013.01); A61Q 5/06 (2013.01); A61K 8/0241 (2013.01); A61K 2800/412 (2013.01); A61K 2800/413 (2013.01); A61K 2800/594 (2013.01); A61K 2800/623 (2013.01)

(58) Field of Classification Search
None
See application file for complete search history.

(56) References Cited

U.S. PATENT DOCUMENTS

| | | |
|---|---|---|
| 2,705,206 A | 3/1955 | Wagner et al. |
| 3,393,155 A | 7/1968 | Schutte et al. |
| 4,049,007 A | 9/1977 | Russell et al. |
| 4,122,029 A | 10/1978 | Gee et al. |
| 4,614,200 A | 9/1986 | Hsiung et al. |
| 4,781,917 A | 11/1988 | Luebbe et al. |
| 4,902,499 A | 2/1990 | Bolish et al. |
| 5,000,937 A | 3/1991 | Grollier et al. |
| 5,362,486 A | 11/1994 | Nandagiri et al. |
| 5,500,216 A | 3/1996 | Julian et al. |
| 5,665,368 A | 9/1997 | Lentini et al. |
| 5,688,831 A | 11/1997 | El-Nokaly et al. |
| 5,911,980 A | 6/1999 | Samour et al. |
| 6,264,933 B1 | 7/2001 | Bodelin et al. |
| 6,315,990 B1 | 11/2001 | Farer et al. |
| 6,464,969 B2 | 10/2002 | De la Poterie et al. |
| 6,534,044 B1 | 3/2003 | Wada et al. |
| 6,683,126 B2 | 1/2004 | Keller et al. |
| 6,685,952 B1 | 2/2004 | Ma et al. |
| 6,709,648 B2 | 3/2004 | Sako et al. |
| 6,800,354 B2 | 10/2004 | Baumann et al. |
| 6,852,389 B2 | 2/2005 | Nun et al. |

(Continued)

FOREIGN PATENT DOCUMENTS

DE  102005052585 A1  5/2007
JP     07215829 A   8/1995

(Continued)

OTHER PUBLICATIONS

U.S. Appl. No. 12/912,816, filed Oct. 27, 2010, Garrison, Mark S.

(Continued)

Primary Examiner — Jyothsna Venkat
(74) Attorney, Agent, or Firm — Brian P. McCloskey

(57) ABSTRACT

Compositions and methods are disclosed for preventing or reducing frizzy appearance of keratin fibers, including hair, and reducing the amount of fly-away strands of hair, particularly in humid conditions, by forming a coating on hair that is resistant to water vapors from the air or surrounding environment. The compositions comprise a combination of a hydrophobic particulate material comprising a hydrophobically surface-modified aluminum oxide and one or more hydrophobic film formers in a cosmetically acceptable vehicle.

11 Claims, No Drawings

(56) References Cited

U.S. PATENT DOCUMENTS

| | | | |
|---|---|---|---|
| 6,946,170 B2 | 9/2005 | Gerber et al. | |
| 7,037,515 B2 | 5/2006 | Kalafsky et al. | |
| 7,056,845 B2 | 6/2006 | Waeber et al. | |
| 7,083,828 B2 | 8/2006 | Muller et al. | |
| 7,150,878 B2 | 12/2006 | Gonzalez et al. | |
| 8,021,651 B2 | 9/2011 | Hentrich et al. | |
| 8,932,569 B2 * | 1/2015 | Garrison et al. | 424/70.12 |
| 8,999,307 B2 * | 4/2015 | Ranade et al. | 424/70.121 |
| 9,005,591 B2 * | 4/2015 | Ranade | A61K 8/11 424/70.12 |
| 2001/0043912 A1 | 11/2001 | Michael | |
| 2002/0197227 A1 | 12/2002 | Scholz | |
| 2004/0009130 A1 | 1/2004 | Detore et al. | |
| 2004/0028709 A1 | 2/2004 | Dueva et al. | |
| 2004/0033451 A1 | 2/2004 | Fujita et al. | |
| 2005/0180943 A1 | 8/2005 | Uehana | |
| 2005/0201961 A1 * | 9/2005 | Lu et al. | 424/63 |
| 2006/0110541 A1 | 5/2006 | Russell et al. | |
| 2006/0110542 A1 | 5/2006 | Dietz et al. | |
| 2008/0066773 A1 | 3/2008 | Anderson et al. | |
| 2008/0085254 A1 | 4/2008 | Nguyen et al. | |
| 2008/0226575 A1 | 9/2008 | Hanna | |
| 2008/0233071 A1 | 9/2008 | Hentrich et al. | |
| 2011/0110991 A1 | 5/2011 | Garrison et al. | |

FOREIGN PATENT DOCUMENTS

| | | |
|---|---|---|
| WO | 2008024308 A2 | 2/2008 |
| WO | 2009/082565 A1 | 7/2009 |
| WO | 2009082565 A1 | 7/2009 |
| WO | 2009111128 A1 | 11/2009 |

OTHER PUBLICATIONS http://www.beauty-advices.com/how-to-control-frizzy-hair-and-how-to-treat-frizzy-hair-properly (2007).

Umberto Giannini, "Perfect Beauty Finishing Cream," (2007).

Mintel, "Weightless Shine Serum," (2007).

* cited by examiner

METHODS AND COMPOSITIONS FOR PREVENTING OR REDUCING FRIZZY APPEARANCE OF HAIR

CROSS-REFERENCE TO RELATED CASES

This application claims priority to U.S. Provisional Patent Application Ser. No. 61/258,651, filed Nov. 6, 2009. This application is a continuation of, and claims priority to, U.S. patent application Ser. No. 12/912,859, filed on Oct. 27, 2010. The entirety of both aforementioned applications are herein incorporated by reference for all purposes.

FIELD OF INVENTION

The present invention relates to methods and compositions for preventing or reducing frizzy appearance of keratin fibers, in particular hair of the head, and reducing the amount of fly-away strands of hair, particularly in humid conditions. More specifically, the invention relates to methods and compositions for forming a coating on hair that is resistant to humidity and water vapors from the air or surrounding environment.

BACKGROUND OF THE INVENTION

Consumers have utilized a number of cosmetic and personal care compositions to enhance the look and feel of keratin fibers, such as the hair. Exposure to humid conditions can cause hair to "poof out," having an excessively expanded volume (i.e., "frizz volume"), or appear frizzy. This frizzy condition of hair often appears unruly and is often characterized with a multiplicity of fly-away strands of hair. Frizzy hair is unsightly and makes it difficult for consumers to control and maintain the hair style. This frizzy condition is particularly pronounced in dry, damaged, or curly hair.

A conventional approach to reducing the frizzy appearance of hair is by applying silicones to the hair. However, these conventional compositions are often impractical, because the large amounts necessary to effectively reduce frizzy appearance of hair can also cause the hair to feel greasy and tacky, thus attracting dirt, and appearing dull and dirty. Conventional compositions may also flake off or leave unsightly residues.

It is therefore an object of the invention to provide an aesthetically pleasing composition for application to keratin fibers, such as hair, which prevents or reduces frizzy appearance and reduces the amount of fly-away strands of hair when the hair is exposed to humid conditions. It is a further object of the invention to provide methods for preventing or reducing frizzy appearance of hair without adversely affecting other aesthetic properties (e.g., appearance, feel, volume, shine, softness) of the hair.

SUMMARY OF THE INVENTION

In accordance with the foregoing objectives and others, the present invention provides methods and compositions for preventing or reducing frizzy appearance of hair. The compositions of the present invention surprisingly provide protection against humid conditions and prevent or reduce frizzy appearance of hair for extended periods of time, e.g., 24 hours, 48 hours, or several days, or semi-permanently, which may last through repeated hair washings. The compositions of the invention may be anhydrous or in the form of emulsions, particularly water-in-oil or water-in-silicone emulsions.

In one aspect of the invention, a method is provided for preventing or reducing frizzy appearance of hair. The method comprises applying to the hair a composition having (a) hydrophobic particulate material comprising a hydrophobically surface-modified aluminum oxide having a median particle size between about 10 nm and about 20 µm, said hydrophobic particulate material comprising from about 0.1% to about 2.0% by weight of said composition; (b) a silicone-based hydrophobic film former comprising from about 0.01% to about 20% by weight of said composition; and (c) a cosmetically acceptable vehicle comprising a silicone fluid having a vapor pressure above about 0.01 mmHg at 20° C. The aggregate weight percentage of all non-volatile water-soluble or water-dispersible organic constituents in the composition is less than 5%, based on the entire weight of the composition. The composition may form a substantially uniform coating on the shafts of the hair fibers. Preferably, the hydrophobic particulate material is surface modified with alkylsilane groups, such as caprylylsilane. More preferably, the hydrophobic particulate material comprises fumed alumina.

In a preferred embodiment, the silicone-based hydrophobic film former may be selected from dimethicone, amodimethicone, dimethiconol, silicone polyurethane, silicone acrylate, or a combination thereof. Specifically, the film former may be a silicone acrylate copolymer, such as is a copolymer comprising a poly(alkyl)acrylate backbone and a dimethicone polymer grafted to an alkyl ester side chain.

The composition may be in the form of a liquid or emulsion. Especially a product intended to be left on the hair and without rinsing, and may be distributed through the hair with a brush, a comb or fingers or sprayed onto the hair. The composition may be applied to the hair when the ambient relative humidity is 85% or above. Alternatively, the composition may be applied to the hair daily. Moreover, the composition when applied to the hair may reduce or prevent the frizzy appearance of hair after at least one shampooing or even after at least two shampooings.

In certain embodiments, the composition may provide a contact angle with a water droplet of between 100° and 150° when applied as a thin film to a glass slide.

These and other aspects of the present invention will become apparent to those skilled in the art after a reading of the following detailed description of the invention, including the appended claims.

DETAILED DESCRIPTION

All amounts provided in terms of weight percentage are relative to the entire composition unless otherwise stated. Unless otherwise provided, the term "alkyl" is intended to embrace straight-chained, branched, or cyclic hydrocarbons, particularly those having from one to 20 carbon atoms, and more particularly $C_{1-12}$ hydrocarbons.

As used herein, the term "keratin fiber" includes hair of the scalp, eyelashes, eyebrows, facial hair, and body hair such as hair of the arms, legs, etc. Keratin fibers are not limited to humans and also include any keratin fibers from a mammal, such as, for example, pet hair and mammalian fur.

The cosmetic compositions of the present invention will generally be anhydrous, although water-containing formulations, such as water-in-oil emulsions are within the scope of the invention. As used herein, the water-in-oil emulsions include water-in-silicone emulsion. When reference is made to the weight % of a component based on the weight of the total composition, the total weight of the composition will be understood to include both the aqueous and oil phases of the emulsion. In the context of the present invention, water is considered a volatile solvent and will thus be excluded from the limitations on hydrophilic components and liquids described herein.

The inventive cosmetic compositions for reducing or preventing frizzy appearance of keratin fibers (e.g., hair) comprises a combination of a hydrophobic particulate material and a silicone-based hydrophobic film former for imparting a coating on keratin fibers. This novel combination has been found to reduced and/or prevent frizzy appearance of hair and reduce the amount of fly-away strands, particularly when the hair is exposed to humid conditions. By humid conditions it is meant that the humidity in the surrounding air is at a level that is capable of inducing frizzy appearance or fly-away strands of hair. In certain embodiments, the compositions are effective to prevent or reduce fizz and reduce fly-away hair at ambient relative humidity (RH) of greater than about 30%, greater than about 40%, greater than about 50%, greater than about 60%, greater than about 70%, greater than about 85%, greater than about 95%, or about 100% RH. It has been observed that hair treated with the inventive combination is more resistant to frizzy appearance than hair treated with an equivalent amount of silicone alone. Without wishing to be bound by any theory, it is believed that the reduction or prevention of frizzy appearance of hair reduction in the amount of fly-away strands of hair is achieved by resisting water vapor from the surrounding air, which is more abundant in humid conditions. It is also believed that the inventive combination provides a synergistic effect for reducing or preventing frizzy appearance of keratin fibers and/or for reducing the amount of fly-away strands of hair. In particular, it is believed that the synergistic effect may be observed in hair exposed to humid conditions. In one embodiment, the synergistic effect may be observed in dry, damaged or curly hair.

Moreover, it is believed that the composition of the present invention may further prevent or reduce frizzy appearance of hair by imparting hydrophobic properties to the hair. It is contemplated that the present invention may impart hydrophilic properties. The contact angle is a measure of the hydrophobicity of the surface and is the angle at which a liquid/vapor interface meets a solid surface. One method for measuring the contact angle is by applying the composition as a film to glass slides and allowing the volatiles to evaporate. The contact angle of the thin film on the glass slide with a drop of water may be suitably measured using a contact angle goniometer. It is contemplated that the compositions of the present invention are capable of providing a film on a surface, after evaporation of volatile solvents, which, in some embodiments, is characterized by a contact angle with a water droplet greater than about 70°, about 80°, about 90°, or about 100° up to about 110°, about 120°, about 130°, about 140°, or about 150°.

A first component of the cosmetic compositions of the invention comprises one or more particulate materials which are either hydrophobic by nature or have been hydrophobically modified by surface treatment or the like. While not wishing to be bound by theory, it is thought that the particulate material provides nano-scale (1 nm to ~1,000 nm) or micro-scale (1 µm to ~200 µm) surface roughness or structure on the film, which repels moisture from the surrounding air by providing protuberances on which water droplets may sit, thereby reducing contact of the water with the surface at large, i.e., reducing surface adhesion.

In one embodiment, the particulate material may comprise at least one hydrophobic particulate material which has a coefficient of dynamic (kinematic) friction, $\mu_k$, greater than 0.5. The particulate material may have a chalky or gritty feel and may have substantially non-spherical shapes. Without wishing to be bound by any theory, it is believed that the substantially non-spherical shape of the high $\mu_k$ (i.e., greater than 0.5) particles provides nano-scale roughness to the particles for repelling moisture. The high drag of the high $\mu_k$, particles also increases the substantivity of the particles against the hair.

Surface roughness can be observed or measured by AFM, SEM, and the like. The coefficient of dynamic friction may be suitably measured using, for example, a Friction Tester (KES-SE) manufactured by Kato Tech Co., LTD using a silicone rubber friction probe to measure a specific amount (e.g., 0.01 g) of sample evenly spread onto a ground quartz plate at a loaded weight of 50 g at 2 mm/sec.

A preferred particulate material according to the invention is hydrophobically modified aluminum oxide ($Al_2O_3$), also known as alumina, particularly fumed (or pyrogenic) alumina. Hydrophobically modified silica ($SiO_2$), including fumed (or pyrogenic) silica (e.g., having a particle size range from about 7 nm to about 40 nm and an aggregate particle size between about 100 and about 400 nm) is also contemplated to be particularly useful. Other notable particulate materials are hydrophobically modified metal oxides, including without limitation titanium dioxide ($TiO_2$), iron oxides (FeO, $Fe_2O_3$ or $Fe_3O_4$), zirconium dioxide ($ZrO_2$), tin dioxide ($SnO_2$), zinc oxide (ZnO), and combinations thereof.

Advantageously, the particulate material may be one which provides additional functionality to the compositions, including for example, ultraviolet (UV) light absorption or scattering, in the case of, for example, titanium dioxide and zinc oxide particulates, or provide aesthetic characteristics, such as color (e.g., pigments), pearlesence (e.g. mica), or the like. The particulate material may be based, for example, on organic or inorganic particulate pigments. Examples of organic particulate pigments include lakes, especially aluminum lakes, strontium lakes, barium lakes, and the like. Examples of the inorganic particulate pigments are iron oxide, especially red, yellow and black iron oxides, titanium dioxide, zinc oxide, potassium ferricyanide ($K_3Fe(CN)_6$), potassium ferrocyanide ($K_4Fe(CN)_6$), potassium ferrocyanide trihydrate ($K_4Fe(CN)_6.3H_2O$), and mixtures thereof. The particulate material may also be based on inorganic fillers such as talc, mica, silica, and mixtures thereof, or any of the clays disclosed in EP 1 640 419, the disclosure of which is hereby incorporated by reference.

In one embodiment, particulate materials are surface-treated to impart a hydrophobic coating thereon. Hydrophobically modified particulates and methods for preparing hydrophobically modified particulates are described in, for example, U.S. Pat. No. 3,393,155 to Schutte et al., U.S. Pat. No. 2,705,206 to Wagner et al., U.S. Pat. No. 5,500,216 to Wagner et al., U.S. Pat. No. 6,683,126 to Keller et al., and U.S. Pat. No. 7,083,828 to Müller et al., U.S. Patent Pub. No. 2006/0110541 to Russell at al., and U.S. Patent Pub. No. 2006/0110542 to Dietz et al., the disclosures of which are hereby incorporated by reference. As used herein, a hydrophobically-modified particle is one which is rendered less hydrophilic or more hydrophobic by surface modification as compared to the particle in the absence of surface modification.

In one embodiment, a hydrophobic particle in accordance with an embodiment of the present invention may be formed from an oxide particle (e.g., a metal oxide, silicon dioxide, etc.) having its surface covered with (e.g., covalently bonded to) non-polar radicals, such as for example alkyl groups, silicones, siloxanes, alkylsiloxanes, organosiloxanes, fluorinated siloxanes, perfluorosiloxanes, organosilanes, alkylsilanes, fluorinated silanes, perfluorinated silanes and/or disilazanes and the like. The surface treatment may be any such treatment that makes the particles more hydrophobic. The surface of the particles may, for example, be covalently or ionically bound to an organic molecule or silicon-based molecule or may be adsorbed thereto, or the particle may be physically coated with a layer of hydrophobic material. There is essentially no limitation on the nature of the hydrophobic treatment and alkyl, aryl, or allyl silanes, silicones, dimethicone, fatty acids (e.g., stearates), polymeric silanes may be mentioned as well as fluoro and perfluoro derivatives thereof. The hydrophobic compound may be attached to the oxide particle through any suitable coupling agent, linker group, or functional group (e.g., silane, ester, ether, etc). The hydrophobic compound comprises a hydrophobic portion which may be selected from, for example, alkyl, aryl, allyl, vinyl, alkyl-aryl, aryl-alkyl, organosilicone, and fluoro- or perfluoro-derivatives thereof. Hydrophobic polymeric coatings including polyurethanes, epoxys and the like, are also contemplated to be useful. U.S. Pat. No. 6,315,990 to Farer, et al., the disclosure of which is hereby incorporated by reference, described suitable fluorosilane coated particulates which are formed by reacting a particulate having a nucleophilic groups, such as oxygen or hydroxyl, with a silicon-containing compound having a hydrocarbyl group substituted by at least one fluorine atom and a reactive hydrocarbyloxy group capable of displacement by a nucleophile. An example of such a compound is tridecafluorooctyltriethoxy silane, available from Sivento, Piscataway, N.J., under the trade name DYNASILANE™ F 8261. A preferred hydrophobic coating according to the invention is prepared by treating an oxide, for example, alumina, with Trimethoxycaprylyl Silane.

Any of the hydrophobically modified particulate materials described in U.S. Pat. No. 6,683,126 to Keller et al., the disclosure of which is hereby incorporated by reference herein, are also contemplated to be useful, including without limitation those obtained by treating an oxide material (e.g., $SiO_2$, $TiO_2$, etc.) with a (perfluoro)alkyl-containing compound that contains at least one reactive functional group that undergoes a chemical reaction with the near-surface OH groups of the oxide support particle, including for example hexamethyldisilazane, octyltrimethoxysilane, silicone oil, chlorotrimethylsilane, and dichlorodimethylsilane.

In one particular preferred embodiment, the particulate material is a fumed (or pyrogenic) alumina or a fumed (or pyrogenic) silica which is surface-functionalized with alkylsilyl, fluoro-alkylsilyl, or perfluoro-alkylsilyl groups, preferably with alkylsilyl groups (i.e., surface treated with alkylsilanes). Typically, the alkylsilyl groups will comprise $C_{1-20}$ hydrocarbons (more typically $C_{1-8}$ hydrocarbons) which are optionally fluorinated or perfluorinated. Such groups may be introduced by reacting at the particle surface with silanes such as $C_{1-12}$-alkyl-trialkoxysilanes (e.g., $C_{1-12}$-alkyl-trimethoxysilanes or $C_{1-12}$-alkyl-triethoxysilanes). Preferably, the particle surface is functionalized with alkylsilyl groups (i.e., surface treated with alkylsilanes). More preferably, the particle surface is functionalized and surface modified with octylsilyl groups, also known as caprylylsilyl groups, introduced by reacting the particles with, octylsilanes (or caprylylsilanes), for example, trimethoxycaprylylsilane or triethoxycaprylylsilane. Such particles are commonly referred to as octylsilane treated. In another embodiment, the oxide particle has been surface treated with a fluoroalkylsilane, and in particular a perfluoroalkylsilane, such as a $C_{1-20}$ perfluoroalkylsilane, or more typically a $C_{1-12}$ perfluoroalkylsilane, including an exemplary embodiment wherein the oxide particle is surface-treated with a $C_8$ perfluoroalkylsilane. The pigments may be prepared by treating the oxide particle with a trialkoxyfluoroalkylsilane, such as Perfluorooctyl Triethoxysilane (INCI). Because the particles are preferably fumed (or pyrogenic), the primary particle size will typically be very small, i.e., on the order of 5 nm to about 30 nm. The specific surface area of these particulate materials will typically, but not necessarily, range from about 50 to about 300 m$^2$/g, more typically, from about 75 to about 250 m$^2$/g, and preferably from about 100 to about 200 m$^2$/g. A suitable hydrophobically modified alumina particulates include fumed aluminum oxide treated with octylsilane (obtained by reacting trimethoxyoctylsilane with fumed alumina), such as AEROXIDE® Alu and AEROXIDE™ ALU C805 from Evonik Industries. That product is believed to have an average primary particle size of about 13 nm (nanometers) and a specific surface area (SSA) of about 100±15 m$^2$/g. Typically, the alumina or hydrophobically-modified alumina has not been calcined, by which is meant that the alumina has not been heated to a high temperature, for example, at a temperature above 1000° C. to expel volatile impurities in the crude metal oxide. Preferably, the particulate material is substantially free of calcined alumina, by which is meant that calcined alumina is not deliberately added to the particulate material and the amounts are so low as to not have a measurable impact on the performance, look or feel of the composition. More preferably, the particulate material is free of calcined alumina.

Additional particles may be included, such as hydrophobically modified fumed silica. When present, suitable hydrophobically modified fumed silica particles include, but are not limited to AEROSIL™ R 202, AEROSIL™ R 805, AEROSIL™ R 812, AEROSIL™ R 812 S, AEROSIL™ R 972, AEROSIL™ R 974, AEROSIL™ R 8200, AEROXIDE™ LE-1, AEROXIDE™ LE-2, and AEROXIDE™ LE-3 from Evonik/Degussa Corporation of Parsippany, N.J., which are believed to be hydrophobic fumed silicas, surface-functionalized with alkylsilyl groups for hydrophobicity and a specific surface area (SSA) of about 160±30 m2/g, about 220±30 m2/g, and 100±30 m2/g, respectively. The hydrophobically modified silica materials described in U.S. Patent Pub. 2006/0110542 to Dietz et al., incorporated herein by reference, are also contemplated to be particularly suitable. Other optional particulates include the particulate silicone wax sold under the trade name Tegotop™ 105 (Degussa/Goldschmidt Chemical Corporation) and the particulate vinyl polymer sold under the name Mincor™ 300 (BASF). While silica ($SiO_2$) and hydrophobically-modified silicas are contemplated to be useful in some embodiments, in other embodiments the compositions will be substantially free of silica or hydrophobically-modified silica. By substantially free of silica or hydrophobically-modified silica means that these components comprise less than about 2%, preferably less than about 1%, and more preferably less than about 0.5% by weight of the one or more particulate materials. In other embodiments the compositions will be free of silica or hydrophobically modified silica. By "free of" is meant that none is deliberately added and any amounts present will be so low as to not impact the look, feel or performance of the composition.

The one or more particulate materials may also comprise particulate organic polymers such as polytetrafluoroethylene, polyethylene, polypropylene, nylon, polyvinyl chloride, and the like which have been formed into fine powders. Alternatively, the particulate material may be a microcapsule comprising any of the shell materials described in U.S. Patent Pub. 2005/0000531, the disclosure of which is hereby incorporated by reference herein.

The one or more particulate materials will typically be in the form of a powder having a median particle size between about 1 nm (nanometers) and about 1 mm (millimeters), more typically between about 5 nm and about 500 µm (micrometer), preferably between about 7 nm and about 1 µm, more preferably between about 10 nm and about 5 µm, about 20 µm, about 50 µm or about 100 µm. Where more than one particulate material is employed (e.g., modified $TiO_2$ and/or modified $SiO_2$), the median particle size of each powder is preferably within the foregoing ranges.

Particulate materials having median particle sizes above about 1 mm may be too large, unless the particle itself contains surface roughness in the appropriate size range. For example, surface treatment of a larger particle with a polymer chain in the 20 nm range may provide acceptable surface roughness. Roughness of the resulting films may be characterized by the size of the primary particle, by the size of agglomerated particles in the aggregate, or by the distribution of particle sizes.

Typically, the one or more particulate material will typically comprise from about 0.01% to about 10% by weight of the total composition, more typically from about 0.1% to about 5%, preferably from about 0.1% to about 2.0%, more preferably from about 0.25% to about 2.0% by weight of the composition, and most preferably from about 0.4% to about 1.5%. In certain embodiments, the one or more particulate material may comprise about 0.4%, about 0.5%, about 0.6%, about 0.67%, about 0.7%, about 0.75%, about 0.8%, about 0.9%, about 1.0%, about 1.25% and about 1.5% by weight of the composition.

In some embodiments, the particulate material may comprise more than about 5%, more than about 10%, more than about 15%, more than about 20%, more than about 25%, more than about 30%, more than about 35%, more than about 40%, more than about 45%, more than about 50%, more than about 55%, more than about 60%, more than about 65%, more than about 70%, more than about 75%, more than about 80%, more than about 85%, more than about 90%, or more than about 95% by weight of octylsilyl-functionalized fumed alumina.

A second component of the composition of the invention comprises one or more film formers. The film former preferably comprises a hydrophobic material. The hydrophobic film former may be any hydrophobic film former suitable for use in a cosmetic composition including, but not limited to, hydrophobic film-forming polymers. The term film-forming polymer may be understood to indicate a polymer which is capable, by itself or in the presence of at least one auxiliary film-forming agent, of forming a continuous film which adheres to a surface and functions as a binder for the particulate material. The term "hydrophobic" film-forming polymer will typically refer to a polymer with a solubility in water at 25° C. of less than about 1% by weight or one in which the monomeric units of the polymer individually have a solubility in water of less than about 1% by weight at 25° C. Alternatively, a "hydrophobic" film forming polymer may be said to be one which partitions predominately into the octanol phase when shaken with a mixture of equal volumes of water and octanol. By predominately is meant more the 50% by weight, but preferably more than 75% by weight, more preferably more than 95% by weight will partition into the octanol phase. The film former is preferably silicone based. By silicone based is meant that the hydrophobic film former comprises at least one silicone moiety, such as, for example, dimethicone, amodimethicone, dimethiconol, silicone polyurethane, silicone acrylate or combinations thereof. Without wishing to be bound by any theory, it is believed that the reduction or prevention of frizzy appearance of hair and for reducing the amount of fly-away strands of hair is achieved by the hydrophobic film former binding the hydrophobic particulate material in an aggregate structure, analogous to a brick and mortar wall, and thereby improving the water vapor resistance properties of hair treated with the inventive composition.

The film formers can be either natural or synthetic, polymeric or non polymeric, resins, binders, with low or high molar mass. Polymeric film formers can be either natural or synthetic, addition or condensation, homochain or heterochain, monodispersed or polydispersed, organic or inorganic, homopolymers or copolymers, linear or branched or crosslinked, charged or uncharged, thermoplastic or thermoset, elastomeric, crystalline or amorphous or both, isotactic or syndiotactic or atactic.

Polymeric film formers include polyolefins, polyvinyls, polacrylates, polyurethanes, silicones, silicone acrylates, polyamides, polyesters, fluoropolymers, polyethers, polyacetates, polycarbonates, polyimides, rubbers, epoxies, formaldehyde resins, and homopolymers and copolymers of and of the foregoing.

Suitable hydrophobic (lipophilic) film-forming polymers include, without limitation, those described in U.S. Pat. No. 7,037,515 to Kalafsky, et al.; U.S. Pat. No. 6,685,952 to Ma et al.; U.S. Pat. No. 6,464,969 to De La Poterie, et al.; U.S. Pat. No. 6,264,933 to Bodelin, et al.; U.S. Pat. No. 6,683,126 to Keller et al.; and U.S. Pat. No. 5,911,980 to Samour, et al., the disclosures of which are hereby incorporated by reference.

Copolymers comprising one or more blocks selected from styrene (S), alkylstyrene (AS), ethylene/butylene (EB), ethylene/propylene (EP), butadiene (B), isoprene (I), acrylate (A) and methacrylate (MA), or a combination thereof, are contemplated to be suitable hydrophobic film formers. Particular mention is made of Ethylene/Propylene/Styrene and Butylene/Ethylene/Styrene copolymer including those sold under the trade name Versagel MD 1600 from Penreco as Gellants in isododecane (IDD).

Special mention may be made of polyalkylenes, and in particular $C_2$-$C_{20}$ alkene copolymers, such as polybutene; alkylcelluloses with a linear or branched, saturated or unsaturated $C_1$-$C_8$ alkyl radical, such as ethylcellulose and propylcellulose; copolymers of vinylpyrrolidone (VP) and in particular copolymers of vinylpyrrolidone and of $C_2$ to $C_{40}$ and better still $C_3$ to $C_{20}$ alkene, including the copolymers of vinyl pyrollidone with eicosene or dodecane monomers sold under the tradenames Ganex V 220 and Ganex V 216 Polymers (ISP Inc. of Wayne, N.J.); polyanhydride resins such as those available from Chevron under the trade name PA-18; copolymers derived from maleic anhydride and $C_3$ to $C_{40}$ alkenes such as octadecene-1; polyurethane polymers, such as Performa V 825 (New Phase Technologies) and those disclosed in U.S. Pat. No. 7,150,878 to Gonzalez, et al., incorporated by reference herein; and polymers and copolymers made from esters of vinylic acid monomers, including without limitation (meth)acrylic acid esters (also referred to as (meth)acrylates), for example, alkyl (meth)acrylates, wherein the alkyl group is chosen from linear, branched and cyclic ($C_1$-$C_{30}$) alkyls, such as, for example, ($C_1$-$C_{20}$) alkyl (meth)acrylates, and further still ($C_6$-$C_{10}$) alkyl (meth)acrylates. Among the alkyl (meth) acrylates which may be mentioned are those chosen from methyl methacrylate, ethyl methacrylate, butyl methacrylate, isobutyl methacrylate, 2-ethylhexyl methacrylate, lauryl methacrylate, and the like. Among the aryl (meth) acrylates which may be mentioned are those chosen from benzyl acrylates, phenyl acrylate, and the like. The alkyl group of the foregoing esters may be chosen, for example, from fluorinated and perfluorinated alkyl groups, that is to say that some or all of the hydrogen atoms of the alkyl group are replaced with fluorine atoms. Mention may also be made of amides of the acid monomers such as (meth)acrylamides, for example, N-alkyl(meth)acrylamides, such as ($C_1$-$C_{20}$) alkyls, including without limitation, N-ethylacrylamide, N-t-butylacrylamide, N-t-octylacrylamide and N-undecylacrylamide. Vinyl polymers for the hydrophobic film-forming polymer may also result from the homopolymerization or copolymerization of at least one monomer chosen from vinyl esters, olefins (including fluoroolefins), vinyl ethers, and styrene monomers. For example, these monomers may be copolymerized with at least one of acid monomers, esters thereof, and amides thereof, such as those mentioned above. Non-limiting examples of vinyl esters which may be mentioned are chosen from vinyl acetate, vinyl neodecanoate, vinyl pivalate, vinyl benzoate and vinyl t-butylbenzoate. Among the olefins which may be mentioned are those chosen, for example, from ethylene, propylene, butene, isobutene, octene, octadecene, and polyfluorinated olefins chosen, for example, from tetrafluoroethylene, vinylidene fluoride, hexafluoropropene and chlorotrifluoroethylene. Styrene monomers which may be mentioned are chosen, for example, from styrene and alpha-methylstyrene. The list of monomers given is not limiting, and it is possible to use any monomer known to those skilled in the art which falls within the categories of acrylic and vinyl monomers which result in hydrophobic films. In this regard, particular mention may be made of the silicone acrylate copolymers, in particular copolymers comprising a poly(alkyl)acrylate backbone and a dimethicone polymer grafted to an alkyl ester side chain, such as the commercially available film former Cyclopentasiloxane (and) Acrylates/Dimethicone Copolymer (KP-545, Shin-Etsu Chemical Co., Ltd) and Methyl Trimethicone (and) Acrylates/dimethicone Copolymer (KP-549, Shin-Etsu Chemical Co., Ltd.)

Other film formers known in the art can be used advantageously in the composition. These include acrylate copolymers, acrylates $C_{12-22}$ alkyl methacrylate copolymer, acrylate/octylacrylamide copolymers, acrylate/VA copolymer, amodimethicone, AMP/acrylate copolymers, behenyl/ isostearyl, butylated PVP, butyl ester of PVM/MA copolymers, calcium/sodium PVM/MA copolymers, dimethicone, dimethicone copolymers, dimethicone/mercaptopropyl methicone copolymer, dimethicone propylethylenediamine behenate, dimethiconol ethylcellulose, ethylene/acrylic acid copolymer, ethylene/MA copolymer, ethylene/VA copolymer, fluoro $C_{2-8}$ alkyldimethicone, $C_{30-38}$ olefin/isopropyl maleate/MA copolymer, hydrogenated styrene/butadiene copolymer, hydroxyethyl ethylcellulose, isobutylene/MA copolymer, methyl methacrylate crosspolymer, methylacryloyl ethyl betaine/acrylates copolymer, octadecene/MA copolymer, octadecene/maleic anhydride copolymer, octylacrylamide/acrylate/butylaminoethyl methacrylate copolymer, oxidized polyethylene, perfluoropolymethylisopropyl ether, polyethylene, polymethyl methacrylate, polypropylene, PVM/MA decadiene crosspolymer, PVM/MA copolymer, PVP, PVP/decene copolymer, PVP/eicosene copolymer, PVP/hexadecene copolymer, PVP/MA copolymer, PVP/VA copolymer, sodium acrylate/vinyl alcohol copolymer, stearoxy dimethicone, stearoxytrimethylsilane, stearyl alcohol, stearylvinyl ether/MA copolymer, styrene/DVB copolymer, styrene/MA copolymer, tricontanyl PVP, trimethylsiloxysilicate, VA/crotonates copolymer, VA/crotonates/vinyl proprionate copolymer, VA/butyl maleate/ isobornyl acrylate copolymer, vinyl caprolactam/PVP/ dimethylaminoethyl methacrylate copolymer, and vinyldimethicone.

Additional non-limiting representatives of hydrophobic film-forming polymers include at least one polycondensate chosen from polyurethanes, polyurethane-acrylics, polyurethane-polyvinylpyrrolidones, polyester-polyurethanes, polyether-polyurethanes, polyureas and polyurea/polyurethanes. The polyurethanes may be for example, at least one chosen from aliphatic, cycloaliphatic, and aromatic polyurethanes, polyureaurethanes, and polyurea copolymers comprising at least one of: at least one sequence of at least one aliphatic polyester origin, cycloaliphatic polyester origin, and aromatic polyester origin at least one branched and unbranched silicone sequence, for example, from polydimethylsiloxane and polymethylphenylsiloxane, and at least one sequence comprising fluorinated groups. Additional non-limiting representatives of polycondensates may be chosen from polyesters, polyesteramides, fatty-chain polyesters, polyamides resins, epoxyester resins, arylsulphonamide-epoxy resins, and resins resulting from the condensation of formaldehyde with an arylsulphonamide.

The hydrophobic film may also be formed in situ by employing a resin which cures after application to the skin, nails, or hair, including for example, a polydimethylsiloxane film formed by in situ hydrosilation of a hydrosilane and an olefinic-substituted siloxane or by in situ polycondensation of alkoxy-functionalized siloxanes.

Preferred polymeric film formers include silicone polymers, acrylates, alkyl acrylates, polyurethanes, fluoropolymers such as Fluomer (polyperfluoroperhydrophenanthrene) or Flutec PP3 available from F2 chemicals, and silicone acrylates such as acrylates/dimethicone copolymers sold under the trade names KP-545 or KP 550 (Shin-Etsu). Suitable film formers include, but are not limited to, Amino Bispropyl Dimethicone, Aminopropyl Dimethicone, Amodimethicone, Amodimethicone Hydroxystearate, Behenoxy Dimethicone, $C_{30-45}$ Alkyl Dimethicone, $C_{24-28}$ Alkyl Dimethicone, $C_{30-45}$ Alkyl Methicone, Cetearyl Methicone, Cetyl Dimethicone, Dimethicone, Dimethoxysilyl Ethylenediaminopropyl Dimethicone, Hexyl Methicone, Hydroxypropyldimethicone, Stearamidopropyl Dimethicone, Stearoxy Dimethicone, Stearyl Methicone, Stearyl Dimethicone and Vinyl Dimethicone. Particularly preferred are silicone polymers, including Methicone (as described by CTFA Monograph No. 1581, which is incorporated herein by reference), Dimethicones (as described by CTFA Monograph No. 840, which is incorporated herein by reference) and Amodimethicones as described by CTFA Monograph No. 189, which is incorporated herein by reference). All CTFA Monographs provided herein are found in the International Cosmetic Ingredient Dictionary and Handbook, $12^{th}$ Edition (2008), and are hereby incorporated by reference.

In one embodiment of the invention, the compositions include a silicone gum. Suitable silicone gums will typically have a molecular weight of from about 200,000 to about 600,000. Specific examples include polydimethylsiloxane, (polydimethylsiloxane) (methylvinylsiloxane) copolymer, poly(dimethylsiloxane) (diphenyl) (methylvinylsiloxane) copolymer, dimethiconol, fluorosilicone, dimethicone, or mixtures thereof. In a preferred embodiment, the film forming silicone gum is a high molecular weight Dimethicone. The high molecular weight Dimethicones have high viscosities and are commonly referred to as dimethicone gums. The viscosity of the silicone gum may be, without limitation, form about 500,000 centistokes to about 100 million centistokes measured at 25° C. The high molecular weight Dimethicones are commercially available in combination with lower molecular weight silicones or with volatile silicones, which makes the high molecular weight Dimethicones easier to handle. A suitable mixture containing high molecular weight Dimethicone (MW approx 500,000) is commercially available from Momentive under the trade name SF 1214.

In another preferred embodiment, the film forming polymer is a silicone acrylate, such as that having the CTFA Monograph No. 10082 and the INCI name Acylates/Dimethicone. This polymer is commercially available from Shin-Etsu Chemical Co., Ltd. under the trade name KP-544 and comprises grafted copolymers with an acrylic polymer backbone and dimethylpolysiloxane side chains. The same polymer is commercially available in a variety of different solvents including Isopropyl Alcohol (KP-541), Butyl Acetate (KP-543), Cyclopentasiloxane (KP-545), Methyl Trimethicone (KP-549), and Isododecane (KP-550).

In another embodiment, the film forming polymer may be a silicone urethane, such as that having the INCI Name Bis-Hydroxypropyl Dimethicone/SMDI Copolymer and the INCI Monograph ID No. 22006. This polymer is commercially available from Siltech Corp. under the trade name SILMER UR-5050, which comprises the polymer in Isododecane.

Other film formers that may be employed include, without limitation, natural, mineral and/or synthetic waxes. Natural waxes are those of animal origin, including without limitation beeswax, spermaceti, lanolin, and shellac wax, and those of vegetable origin, including without limitation carnauba, candelilla, bayberry, and sugarcane wax, and the like. Mineral waxes contemplated to be useful include, without limitation ozokerite, ceresin, montan, paraffin, microcrystalline, petroleum, and petrolatum waxes. Synthetic waxes include, for example, Fischer Tropsch (FT) waxes and polyolefin waxes, such as ethylene homopolymers, ethylene-propylene copolymers, and ethylene-hexene copolymers. Representative ethylene homopolymer waxes are commercially available under the tradename POLYWAX® Polyethylene (Baker Hughes Incorporated). Commercially available ethylene-α-olefin copolymer waxes include those sold under the tradename PETROLITE® Copolymers (Baker Hughes Incorporated). Another wax that is suitable is dimethiconol beeswax available from Noveon as ULTRABEE™ dimethiconol ester.

In some embodiments, it may be desirable to add a hydrophilic or water-soluble film former (e.g., cellulosics, polysaccharides, polyquaterniums (such as polyquaternium-37 (INCI), etc.) to the composition to improve spreading, emulsion stability, aesthetic look and feel, etc. While less preferred, it is within the scope of the invention to include such hydrophilic or water-soluble film formers. There is no restriction on the amount of hydrophilic or water-soluble film former, although at high levels (e.g., greater than 20% by weight based on the total weight of film former) it may be necessary to increase the ratio of hydrophobic particulate to film former to counter the reduction in surface hydrophobicity. In some embodiments, the collective weight percentage of hydrophilic or water-soluble film formers will be less than about 20%, preferably less than about 15%, more preferably less than about 10%, and more preferred still, less than about 5% by weight based on the total weight of all film formers. In a preferred embodiment, hydrophilic film formers will comprise less than about 2% by weight of the total weight of film formers in the composition. In one embodiment, the composition is substantially free of water-soluble film formers by which is meant that the composition comprise less than 2% by weight, preferably, less than 1% by weight, and more preferred still, less than 0.5% by weight of the one or more film formers. In one embodiment the composition does not contain a hydrophilic film former.

Combinations of any of the foregoing film formers are also contemplated to be suitable, including combinations or polymeric and non-polymeric film formers.

The film former will comprise from about 0.01% to about 20% by weight of the composition, and more typically will comprise from about 0.25% to about 15%, and preferably from about 1 to 12%, more preferably from 1.5% to about 10%, and more preferred still about 3% to about 8% by weight of the composition. Generally, the weight ratio of the one or more hydrophobic particulate material to one or more film formers will be from about 1:1 to about 1:100, about 1:1.25 to about 1:75, about 1:1.5 to about 1:50, about 1:1.75 to about 1:25, or about 1:2 to about 1:10. Mention may be made of the following ratios of one or more hydrophobic particulate material to one or more film formers: about 1:20, about 1:15, about 1:10, about 1:9, about 1:8, about 1:7, about 1:6, about 1:5, about 1:4, about 1:3, about 1:2, about 1:1.5 and about 1:1.

In certain embodiments, the composition will comprise a silicone acrylate film former in addition to a silicone gum film former. The silicone acrylate film former and the silicone gum film former may each independently comprise from about 0.01% to about 20% by weight of the composition, and more typically will comprise from about 0.25% to about 15%, and preferably from about 1.0% to about 10%, and more preferably, from 1.5% to about 8%, and more preferred still about 3% to about 5% by weight of the composition.

The inventive compositions will typically comprise a cosmetically acceptable vehicle. By "cosmetically acceptable" is meant that the vehicle is safe for contact with a human integument. The vehicle may comprise a liquid, comprising a single phase, a dual-phase system, or an emulsion. Emulsions include oil-in-water, silicone-in-water, water-in-oil, water-in-silicone, and the like. Where the product is intended as a spray, it may be desirable to employ a single phase vehicle, or a dual phase vehicle comprising an aqueous phase and an oil phase, the oil phase comprising a silicone oil. When formulated as an emulsion, an emulsifier is typically included. In other embodiments, the composition is substantially free or free of an emulsifier. By substantially free of an emulsifier is meant that no emulsifier is deliberately added to the composition and the amounts present, if any, are so low as to not have a measurable impact on the stability of an emulsion.

In one embodiment, the vehicle may comprise a volatile solvent. Typically, a volatile solvent may have a vapor pressure of above about 0.01 mmHg at 20° C. Volatile solvents may include volatile $C_{5-12}$ hydrocarbons (e.g., isododecane), aromatic hydrocarbons (e.g., xylenes, toluene, etc.), ketones (e.g., actetone, methylethyl ketone, etc.), ethers (e.g., diethyl ether, methylethyl ether, etc.), perfluorohydrocarbons, hydrofluoroethers, Freons, volatile silicones (e.g., cyclopentasiloxane), lower alcohols (e.g., ethanol, isopropyl alcohol, etc.), esters of acetic acid (e.g., ethylacetate, butylacetate, etc.) and the like. Preferred volatile solvents will be cosmetically acceptable.

Volatile silicones are a preferred volatile solvent. By volatile silicone is meant that the oil readily evaporates at ambient temperatures. Typically, volatile silicone oils will exhibit a vapor pressure ranging from about 1 Pa to about 2 kPa at 25° C.; will preferably have a viscosity of from about 0.1 to about 10 centistokes, preferably about 5 centistokes or less, more preferably about 2 centistokes or less, at 25° C.; and will boil at atmospheric pressure at from about 35° C. to about 250° C. Volatile silicones include cyclic and linear volatile dimethylsiloxane silicones, including 0.5 cst dimethicone, 0.65 cst dimethicone, 1 cst dimethicone, and 1.5 cst dimethicone. In one embodiment, the volatile silicones may include cyclodimethicones, including tetramer (D4), pentamer (D5), and hexamer (D6) cyclomethicones, or mixtures thereof. Suitable dimethicones are available from Dow Corning under the name Dow Corning 200® Fluid and have viscosities ranging from 0.65 to 5 centistokes. Suitable non-polar, volatile liquid silicone oils are disclosed in U.S. Pat. No. 4,781,917, herein incorporated by reference in its entirety. Additional volatile silicones materials are described in Todd et al., "Volatile Silicone Fluids for Cosmetics," Cosmetics and Toiletries, 91:27-32 (1976), herein incorporated by reference in its entirety. Linear volatile silicones generally have a viscosity of less than about 5 centistokes at 25° C., whereas the cyclic silicones have viscosities of less than about 10 centistokes at 25° C. Examples of volatile silicones of varying viscosities include Dow Corning 200, Dow Corning 244, Dow Corning 245, Dow Corning 344, and Dow Corning 345, (Dow Corning Corp.); SF-1204 and SF-1202 Silicone Fluids (G.E. Silicones), GE 7207 and 7158 (General Electric Co.); and SWS-03314 (SWS Silicones Corp.). Linear, volatile silicones include low molecular weight polydimethylsiloxane compounds such as methyltrimethicone, trisiloxane, hexamethyldisiloxane, octamethyltrisiloxane, decamethyltetrasiloxane, and dodecamethylpentasiloxane to name a few. Particularly preferred volatile silicones of the present invention include cyclomethicone tetramer, cyclomethicone pentamer, cyclomethicone hexamer, trisiloxane, methyl trimethicone or combinations thereof.

Lower alcohol solvents, including methanol, ethanol (also known as ethyl alcohol), propanol, and isopropanol, are also contemplated to be useful. Ethanol is particularly preferred due to its high volatility and low toxicity. Preferably, the ethanol is anhydrous ethanol, such as SD Alcohol 40 from Exxon. In other embodiments, the compositions comprises less than about 50%, less than about 40%, less than about 30%, less than about 20%, less than about 10%, or less than about 5% by weight ethanol. In some embodiments, the compositions comprises less than about 2.5%, less than about 1%, or less than about 0.5% by weight ethanol. In other embodiments, the compositions are substantially free of ethanol, by which is meant that no ethanol is deliberately added and the amounts present, if any, are so low as to not have a measurable impact on the look, feel, or performance of the product. In another embodiment, the composition is free of ethanol.

Among the volatile $C_{5-12}$ hydrocarbons, special mention may be made of isododecane which is available under the trade name Permethyl-99A (Presperse Inc.). Suitable fluorinated solvents include, without limitation, perfluoroethers, perfluorodecalin, perfluoromethyldecalin, perfluorohexane, perfluoromethylcyclohexane, perfluorodimethylcyclohexane, perfluoroheptane, perfluorooctane, perfluorononane, and perfluoromethylcycopentane, for example.

In a preferred embodiment, the solvent will comprise a combination of a volatile silicone, preferably cyclomethicone pentamer, and anhydrous ethanol. Preferably, the volatile silicone (cyclomethicone pentamer) will comprise from about 1% to about 99% and the ethanol will comprise from about 1% to about 99% by weight of the solvent system. More particularly, the volatile silicone (cyclomethicone pentamer) will comprise from about 50% to about 99% and the ethanol will comprise from about 1% to about 50% by weight of the solvent system. In a preferred embodiment, volatile silicone (cyclomethicone pentamer) will comprise from about 70% to about 90% and ethanol will comprise from about 10% to about 30% by weight of the solvent system.

In a further embodiment, the compositions according to the invention will comprise ethanol, preferably anhydrous, in combination with one or more solvents having a vapor pressure at 25° C. which is less than the vapor pressure of ethanol. In another embodiment, the compositions according to the invention will comprise ethanol, preferably anhydrous, in combination with one or more solvents having a vapor pressure at 25° C. which is greater than the vapor pressure of ethanol.

Anhydrous Formulations

The compositions of the invention may be provided as anhydrous or substantially anhydrous formulations. By "substantially anhydrous" is mean that the weight percentage of water in the composition is less than about 0.5%, preferably less than 0.25%, and most preferably less than about 0.1% by weight. Typically, the anhydrous compositions are substantially free of water by which is meant that water is not deliberately added to the compositions and the level of water is no more than would be expected based on the absorption of water from the air. The anhydrous composition will typically comprise a volatile hydrophobic solvent, such as volatile hydrocarbons, volatile silicones, and the like.

Water-in-Oil Emulsions

The compositions according to the invention may be formulated as water-in-oil emulsions. These emulsions comprise an oil-containing continuous phase and an aqueous discontinuous phase.

The oil-containing phase will typically comprise from about 10% to about 99%, from about 20% to about 85%, or from about 30% to about 75% by weight, based on the total weight of the composition, and the aqueous phase will typically comprise from about 1% to about 90%, from about 5% to about 80%, from about 10% to about 70%, or from about 15% to about 60% by weight of the composition. In one embodiment, the oil containing phase and the aqueous phase may comprise approximately equal percentages of the total weight of the emulsion.

The oil-containing phase may be composed of a single oil or mixtures of different oils. Essentially any oil is contemplated to be useful, although highly hydrophobic oils are preferred. Suitable non-limiting examples include vegetable oils; esters such as octyl palmitate, isopropyl myristate and isopropyl palmitate; ethers such as dicapryl ether; fatty alcohols such as cetyl alcohol, stearyl alcohol and behenyl alcohol; isoparaffins such as isooctane, isododecane and isohexadecane; silicone oils such as dimethicones, cyclic silicones, and polysiloxanes; hydrocarbon oils such as mineral oil, petrolatum, isoeicosane and polyisobutene; natural or synthetic waxes; and the like.

Suitable hydrophobic hydrocarbon oils may be saturated or unsaturated, have an aliphatic character and be straight or branched chained or contain alicyclic or aromatic rings. Hydrocarbon oils include those having 6-20 carbon atoms, more preferably 10-16 carbon atoms. Representative hydrocarbons include decane, dodecane, tetradecane, tridecane, and $C_{8-20}$ isoparaffins. Paraffinic hydrocarbons are available from Exxon under the ISOPARS trademark, and from the Permethyl Corporation. In addition, $C_{8-20}$ paraffinic hydrocarbons such as $C_{12}$ isoparaffin (isododecane) manufactured by the Permethyl Corporation having the tradename Permethyl 99A™ are also contemplated to be suitable. Various commercially available $C_{16}$ isoparaffins, such as isohexadecane (having the tradename Permethyl R™) are also suitable. Examples of preferred volatile hydrocarbons include polydecanes such as isododecane and isodecane, including for example, Permethyl-99A (Presperse Inc.) and the $C_7$-$C_8$ through $C_{12}$-$C_{15}$ isoparaffins such as the Isopar Series available from Exxon Chemicals. A representative hydrocarbon solvent is isododecane.

Critically, the emulsions have little or no non-volatile hydrophilic constituents, including some conventional humectants. Components such as glycerin and polyols, including propylene glycol, ethoxydiglycol, glycerin, butylene glycol, pentylene glycol and hexylene glycol should be eliminated or should be kept at levels such that the non-volatile hydrophilic constituents, such as non-volatile water soluble or water-dispersible organic constituents, in the aggregate, do not exceed 15% by weight and preferably will be less than 10%, less than 5%, less than 2%, or less than 1% by weight, based on the entire weight of the composition. Glycerin has been found to be particularly detrimental and should therefore be maintained at levels below 2% by weight, or below 1% by weight, or eliminated altogether.

It has been found that the selection and amount of emulsifier is important for obtaining films which provide water vapor resistant properties. Because the emulsifier itself may be deleterious to the formation of a water vapor resistant film or adversely affect the durability of the performance through repeated hair washings, the compositions preferably have the lowest level of emulsifier capable of producing a stable emulsion. The amount of emulsifier will typically be from about 0.001 to about 10% by weight, but preferably will range from about 0.01 to about 5% by weight, more preferably from 0.1 to 3%, and most preferably about 0.25 to about 1% by weight, based upon the total weight of the composition. In other embodiments, the emulsifier may be absent. In compositions where the emulsifier is extremely low or absent, the composition may be of the "shake well" type such that the composition forms a transient emulsion when it is vigorously mixed or shaken, and separates into two distinct phases when left undisturbed over a period of time in a container.

For water in oil emulsions, the emulsifier itself should be of low Hydrophilic-Lipophilic Balance (HLB), preferably below 10, more preferably below 8.5. While combinations of more than one emulsifier are contemplated to be within the scope of the invention, each such emulsifier, individually, should be of low HLB. Therefore, the use of high and low HLB emulsifiers, which in combination give low HLB (e.g., less than 8.5), is less desirable because even if the combined HLB of the system is below 8.5, the contribution of the higher HLB emulsifier will be detrimental to the formation of a water vapor resistant film. If present, the amount of emulsifier having an HLB above 10 will be less than 1% by weight, more preferably less than 0.5% by weight, and more preferred still, less than 0.2% by weight.

Where the emulsifier is of the polyethoxylated type (e.g., polyoxyethylene ethers or esters) comprising chains of the form —$(CH_2CH_2O)_n$—, it is preferred that n be less than 20, more preferably less than 10, most preferably less than 5. Propoxylated emulsifiers are also contemplated to be suitable. Propoxylated emulsifiers also preferably having less than 20, more preferably less than 10, most preferably less than 5 propylene oxide repeat units.

Emulsifiers that can be used in the composition of the present invention include, but are not limited to, one or more of the following: sorbitan esters; polyglyceryl-3-diisostearate; sorbitan monostearate, sorbitan tristearate, sorbitan sesquioleate, sorbitan monooleate; glycerol esters such as glycerol monostearate and glycerol monooleate; polyoxyethylene phenols such as polyoxyethylene octyl phenol and polyoxyethylene nonyl phenol; polyoxyethylene ethers such as polyoxyethylene cetyl ether and polyoxyethylene stearyl ether; polyoxyethylene glycol esters; polyoxyethylene sorbitan esters; dimethicone copolyols; polyglyceryl esters such as polyglyceryl-3-diisostearate; glyceryl laurate; Steareth-2, Steareth-10, and Steareth-20, to name a few. Additional emulsifiers are provided in the INCI Ingredient Dictionary and Handbook 11th Edition 2006, the disclosure of which is hereby incorporated by reference.

An example of a very low HLB emulsifier contemplated to be suitable according to the invention is Span 83, a sesquiester of monooleate and dioleate at a 2:1 molar ratio which has an HLB of 3.7. Sorbitan monostearate (INCI) is another suitable emulsifier, having an HLB value of 4.7.

The aqueous phase may include one or more additional solvents, preferably volatile solvents, including lower alcohols, such as ethanol, isopropanol, and the like. The volatile solvents, when present in the aqueous phase, will typically comprise from about 0.1% to about 75% by weight of the aqueous phase, more typically up to about 35% by weight, and preferably up to about 15% by weight. The water and optional volatile solvents are contemplated to enhance the formation of a water vapor resistant film because the particulates will tend to be pushed to the surface of the film as the solvents evaporate.

Water-in-Silicone Emulsion

One type of water-in-oil emulsion that has been found to be useful is a water-in-silicone emulsions having a silicone oil-containing continuous phase and an aqueous discontinuous phase.

Typically, water is incorporated into the composition to form a water-in-silicone emulsion for the purpose of dissolving water soluble ingredients into the composition. The water soluble may include water soluble polymer amongst other that impart additional aesthetic benefits, e.g., look and/or feel to the hair. Preferably, the amount of water added to the composition will be at a minimum that is required or necessary to dissolve the desired water soluble ingredient. Alternatively, water may be incorporated into the composition for the purpose of forming a water-in-silicone emulsion and increasing the viscosity of the composition. Preferably, the amount of water introduced is at a minimum amount necessary to achieve the desired viscosity.

The silicone-containing phase will typically comprise from about 10% to about 99%, from about 20% to about 85%, or from about 30% to about 75% by weight, based on the total weight of the composition, and the aqueous phase will typically comprise from about 1% to about 90%, from about 5% to about 80%, from about 10% to about 70%, or from about 15% to about 60% by weight of the composition. In one embodiment, the silicone containing phase and the aqueous phase may comprise approximately equal percentages of the total weight of the emulsion.

Preferably, only the minimum amount of water necessary to achieve the desired functions, such as dissolving water soluble ingredients or increasing viscosity of the composition, should be introduced. For example, if a lotion consistency is desired, and the composition includes low amounts of water soluble polymers in its formula, between 10% and 25% of water will usually suffice. In another example, if a creme consistency is desired for the composition, or if large amounts of water soluble ingredients (e.g., actives/polymers/etc.) are desired, between about 25% and about 50% of water may be necessary. The silicone-containing or oil-containing phase may vary depending on the amount of aqueous phase present in the composition.

The silicone oil phase may include volatile silicone oils, non-volatile silicone oils, and combinations thereof. By volatile silicone oil is meant that the oil readily evaporates at ambient temperatures. Typically, volatile silicone oils will exhibit a vapor pressure ranging from about 1 Pa to about 2 kPa at 25° C.; will preferably have a viscosity of from about 0.1 to about 10 centistokes, preferably about 5 centistokes or less, more preferably about 2 centistokes or less, at 25° C.; and will boil at atmospheric pressure at from about 35° C. to about 250° C.

Volatile silicones useful for the silicone oil phase of the water-in-silicone emulsion include cyclic and linear volatile dimethylsiloxane silicones. In one embodiment, the volatile silicones may include cyclodimethicones, including tetramer (D4), pentamer (D5), and hexamer (D6) cyclomethicones, or mixtures thereof. Particular mention may be made of the volatile cyclomethicone-hexamethyl cyclotrisiloxane, octamethyl-cyclotetrasiloxane, and decamethyl-cyclopentasiloxane. Suitable volatile dimethicones are available from Dow Corning under the name Dow Corning 200® Fluid and have viscosities ranging from about 0.65 to about 5 centistokes. Suitable non-polar, volatile liquid silicone oils are disclosed in U.S. Pat. No. 4,781,917, herein incorporated by reference in its entirety. Additional volatile silicones materials are described in Todd et al., "Volatile Silicone Fluids for Cosmetics", Cosmetics and Toiletries, 91:27-32 (1976), herein incorporated by reference in its entirety. Linear volatile silicones generally have a viscosity of less than about 5 centistokes at 25° C., whereas the cyclic silicones have viscosities of less than about 10 centistokes at 25° C. Examples of volatile silicones of varying viscosities include Dow Corning 200, Dow Corning 244, Dow Corning 245, Dow Corning 344, and Dow Corning 345, (Dow Corning Corp.); SF-1204 and SF-1202 Silicone Fluids (G.E. Silicones), GE 7207 and 7158 (General Electric Co.); and SWS-03314 (SWS Silicones Corp.). Linear, volatile silicones include low molecular weight polydimethylsiloxane compounds such as hexamethyldisiloxane, octamethyltrisiloxane, decamethyltetrasiloxane, and dodecamethylpentasiloxane to name a few.

Non-volatile silicone oils will typically comprise polyalkylsiloxanes, polyarylsiloxanes, polyalkylarylsiloxanes, or mixtures thereof. Polydimethylsiloxanes are preferred non-volatile silicone oils. The non-volatile silicone oils will typically have a viscosity from about 10 to about 60,000 centistokes at 25° C., preferably between about 10 and about 10,000 centistokes, and more preferred still between about 10 and about 500 centistokes; and a boiling point greater than 250° C. at atmospheric pressure. Non limiting examples include dimethyl polysiloxane (dimethicone), phenyl trimethicone, and diphenyldimethicone.

The volatile and non-volatile silicone oils may optionally be substituted will various functional groups such as alkyl, aryl, amine groups, vinyl, hydroxyl, haloalkyl groups, alkylaryl groups, and acrylate groups, to name a few.

The water-in-silicone emulsion is emulsified with a non-ionic surfactant (emulsifier). Suitable emulsifiers include polydiorganosiloxane-polyoxyalkylene block copolymers, including those described in U.S. Pat. No. 4,122,029, the disclosure of which is hereby incorporated by reference. These emulsifiers generally comprise a polydiorganosiloxane backbone, typically polydimethylsiloxane, having side chains comprising $-(EO)_m-$ and/or $-(PO)_n-$ groups, where EO is ethyleneoxy and PO is 1,2-propyleneoxy, the side chains being typically capped or terminated with hydrogen or lower alkyl groups (e.g., $C_{1-6}$, typically $C_{1-3}$). The side chains will preferably comprise 50 EO and/or PO units or less (e.g., $m+n=<50$), preferably 20 or less, and more preferably 10 or less. In addition to the alkoxylated side chain, the silicone emulsifier may also comprise alkyl chains pendant from the silicone backbone. Other suitable water-in-silicone emulsifiers are disclosed in U.S. Pat. No. 6,685,952, the disclosure of which is hereby incorporated by reference herein. Commercially available water-in-silicone emulsifiers include those available from Dow Corning under the trade designations 3225C and 5225C FORMULATION AID; SILICONE SF-1528 available from General Electric; ABIL EM 90 and EM 97, available from Goldschmidt Chemical Corporation (Hopewell, Va.); and the SILWET™ series of emulsifiers sold by OSI Specialties (Danbury, Conn.).

Examples of water-in-silicone emulsifiers include, without limitation, PEG/PPG-18/18 dimethicone (trade name 5225C, Dow Corning), PEG/PPG-19/19 dimethicone (trade name BY25-337, Dow Corning), Cetyl PEG/PPG-10/1 dimethicone (trade name Abil EM-90, Goldschmidt Chemical Corporation), PEG-12 dimethicone (trade name SF 1288, General Electric), lauryl PEG/PPG-18/18 methicone (trade name 5200 FORMULATION AID, Dow Corning), PEG-12 dimethicone crosspolymer (trade name 9010 and 9011 silicone elastomer blend, Dow Corning), PEG-10 dimethicone crosspolymer (trade name KSG-20, Shin-Etsu), and dimethicone PEG-10/15 crosspolymer (trade name KSG-210, Shin-Etsu).

It has been found that the selection and amount of emulsifier is important for obtaining films which provide water vapor resistant properties. Because the emulsifier itself may be deleterious to the formation of a water vapor resistant film or adversely affect the durability of the performance through repeated hair washings, the compositions preferably have the lowest level of emulsifier capable of producing a stable emulsion. The water-in-silicone emulsifiers typically will be present in the composition in an amount from about 0.001% to about 10% by weight, in particular in an amount from about 0.01% to about 5% by weight, and more preferably, below 1% by weight. In other embodiments, the emulsifier may be absent. In compositions where the emulsifier is extremely low or absent, the composition may be of the "shake well" type such that the composition forms a transient emulsion when it is vigorously mixed or shaken, and separating into two distinct phases when left undisturbed over a period of time.

In one embodiment of the invention, the one or more hydrophobic particulate material and the film former are first dispersed or dissolved in the oil or silicone phase of a water-in-oil or water-in-silicone emulsion. The oil or silicone is subsequently mixed with the aqueous phase to form the emulsion. The emulsions will typically have the hydrophobic film formers and any hydrophobic pigments dispersed or dissolved predominantly in the oil or silicone phase.

In some embodiments, it has been found desirable to include one or more agents that enhance the shine of hair treated with the compositions of the invention. The hydrophobic particulate materials, particularly the hydrophobically-modified fumed oxides such as alumina and silica, impart a matte finish to the hair which may be undesirable from a consumers perspective. It has been discovered that shine can be restored to the hair, without sacrificing the water-resistance, by including one of more agents which modify the shine of hair. The shine-enhancing agent is preferably hydrophobic and is also preferably solid at room temperature such that the particulate material does not become covered when the composition is applied to the hair. For example, lens-shaped particles such as hemi-spherical PMMA have been found suitable for imparting shine. One such commercially available material is a hemi-spherical methyl methacrylate crosspolymer sold under the trade name 3D Tech PW (Plain) XP (Kobo). Other suitable shine enhancers include phenylpropyldimethylsiloxysilicate, polybutene, polyisobutene, hydrogenated polyisobutene.

Silicone fluids, such as aryl-substituted siloxanes having high refractive indices are also useful as shine enhancers. Particular mention may be made of Phenyltrimethicone, which is available under the trade names SCI-TEC PTM 100 (ISP) and PDM20 (Wacker-Belsil), and Trimethylsiloxyphenyl Dimethicone (INCI name), which is available under the trade name PDM 1000 (Wacker-Belsil). The PDM20 material has a refractive index of 1.437 at 25° C. The PDM 1000 material has a refractory index of 1.461 at 25° C. Another suitable silicone fluid is trimethylsiloxyphenyl dimethicone. In general, any aryl-substituted silicone having a refractive index of greater than 1.4 at 25° C. is contemplated to be suitable for restoring shine to hair treated with the inventive compositions. Phenyl silicones such as pentaphenyl trimethyl trisiloxane or tetraphenyl tetramethyl trisiloxane, commercially available as HRI fluids from Dow corning HRI, are also useful for enhancing shine. Certain organic compounds, such as octyl methoxy cinnamate, may also be used to enhance shine.

The shine enhancer is typically present from about 0.01% to about 5% by weight of the total composition. More typically, the shine enhancer component will comprise from about 0.05% to about 2.5% by weight of the composition. Preferably, the shine enhancer will comprise from about 0.1% to about 1.5% by weight of the composition, including embodiments wherein the shine enhancer is present at about 0.1%, 0.3%, 0.5%, 0.75%, 1%, 1.25%, or 1.5% by weight of the composition.

In addition to the foregoing, the compositions according to the invention may comprise additional pigments, pearlescents, and/or colorants to combat the white appearance of fumed alumina or fumed silica or otherwise to impart a desired color to the hair, provided that such components do not undesirably detract from the product performance. Inorganic pigments include without limitation titanium dioxide, zinc oxide, iron oxides, chromium oxide, ferric blue, and mica; organic pigments include barium, strontium, calcium or aluminium lakes, ultramarines, and carbon black; colorants include without limitation D&C Green #3, D&C Yellow #5, and D&C Blue #1. Pigments and/or colorants may be coated or surface treated with one or more compatibilizers to aid in dispersion in the solvent. Preferred pigments and/or colorants are those surface treated to render them hydrophobic.

Preferred colorants include Iron Oxides, Black Oxide of Iron, Brown Iron Oxide, CI 77489, CI 77491, CI 77492, CI 77499, Iron Oxide Red 10-34-PC-2045, Pigment Black 11, Pigment Brown 6, Pigment Brown 7, Pigment Red 101, Pigment Red 102, Pigment Yellow 42, Pigment Yellow 43, Red Iron Oxide, Synthetic Iron Oxide, and Yellow Iron Oxide.

Various fillers and additional components may be added. Suitable fillers include without limitation silica, treated silica, talc, zinc stearate, mica, kaolin, Nylon powders such as Orgasol™, polyethylene powder, Teflon™, boron nitride, copolymer microspheres such as Expancel™ (Nobel Industries), Polytrap™ (Dow Corning) and silicone resin microbeads (Tospearl™ from Toshiba), and the like.

Additional pigment/powder fillers include, but are not limited to, inorganic powders such as gums, chalk, Fuller's earth, kaolin, sericite, muscovite, phlogopite, synthetic mica, lepidolite, biotite, lithia mica, vermiculite, aluminum silicate, starch, smectite clays, alkyl and/or trialkyl aryl ammonium smectites, chemically modified magnesium aluminum silicate, organically modified montmorillonite clay, hydrated aluminum silicate, aluminum starch octenyl succinate barium silicate, calcium silicate, magnesium silicate, strontium silicate, metal tungstate, magnesium, silica alumina, zeolite, barium sulfate, calcined calcium sulfate (calcined gypsum), calcium phosphate, fluorine apatite, hydroxyapatite, ceramic powder, metallic soap (zinc stearate, magnesium stearate, zinc myristate, calcium palmitate, and aluminum stearate), colloidal silicone dioxide, and boron nitride; organic powder such as polyamide resin powder (nylon powder), cyclodextrin, polymethylmethacrylate powder (PMMA), copolymer powder of styrene and acrylic acid, benzoguanamine resin powder, poly(ethylene tetrafluoride) powder, and carboxyvinyl polymer, cellulose powder such as hydroxyethyl cellulose and sodium carboxymethyl cellulose, ethylene glycol monostearate; inorganic white pigments such as magnesium oxide; and stabilizers/rheology modifiers, for example, Bentone Gel and Rheopearl TT2. Other useful powders are disclosed in U.S. Pat. No. 5,688,831, the disclosure of which is hereby incorporated by reference.

The aggregate amount of all such additional pigments, colorants, and fillers is not particularly restricted provided that the water vapor resistance and reduction of frizzy appearance of treated hair is not compromised. Typically, all additional pigments, colorants, fillers, etc., if present, will collectively comprise from about 0.1% to about 5% of the total composition, but more typically will comprise from about 0.1% to about 2% by weight of the composition.

The compositions of the invention may optionally comprise other active and inactive ingredients typically associated with hair care products. The nature of these other ingredients and their amounts should preferably be suitable for formulating a stable hair care product which forms a hydrophobic film on keratin fibers. Preferably, these other ingredients include at least one bioactive ingredient for improving the keratin fiber. It is within the skill in the art to choose additional active and/or inactive ingredients for a hair care product. Suitable other ingredients include, but are not limited to, amino acids, antioxidants, chelating agents, colorants, emollients, emulsifiers, excipients, fillers, fragrances, gelling agents, humectants, minerals, moisturizers, photostabilizing agents (e.g., UV absorbers), preservatives, stabilizers, staining agents, surfactants, viscosity and/or rheology modifiers, vitamins, waxes and mixtures thereof. It is contemplated that the inventive hair care product of the present invention can also include anti-dandruff, deodorant, sunscreen and/or antiperspirant ingredients. If present, the levels of such additional components should be judiciously selected so as not to adversely impact the ability of the compositions to reduce or prevent frizzy appearance of hair. Collectively, all such additional components suitably will comprise less than 5% by weight of the composition, but will typically comprise less than about 2% by weight, and will preferably will comprise less than 1% by weight, more preferably less than 0.5% by weight, and ideally less than 0.1% by weight of the total composition.

In one embodiment, the composition will be free or substantially free of cationic hair conditioning agents. By substantially free of cationic hair conditioning agents is meant that the compositions comprise less than 0.5% by weight, preferably, less than 0.25% by weight, and more preferred still, less than 0.1% by weight cationic conditioning agents.

In other embodiments the compositions may contain an amount of cationic (quaternium) ingredients that are anhydrous or have very low level of water, e.g., less than 1% by weight. Suitable quaternium compounds include, without limitation, Polyquaternium-37 (INCI), Cyclopentasiloxane and Silicone Quaternium-18 (INCI), PEG-2 Dimeadowfoamamidoethylmonium Methosulfate and Hexylene Glycol (INCI), and Cetrimonium Chloride (INCI), to name a few. Such quaternium compounds, if present, will typically comprise from about 0.05% to about 1.5% by weight of the total composition, and more typically, from about 0.1% to about 1% by weight.

The composition of the present invention may be formulated in any suitable form, including various rinse-off and leave-in formulations, such as but not limited to shampoos, conditioners, serums, creams, sprays, emulsions, gels, balms, liquids, dispersions, and the like.

In one embodiment, the compositions may be formulated for pump or aerosol delivery to the hair. When formulated for aerosol delivery, a propellant will be included which is suitable for delivery of the composition onto the hair. Suitable propellants include, without limitation, n-butane, isobutane, and isobutane/propane, nitrogen, carbon dioxide, compressed air, nitrous oxide, 1,2-difluoroethane, 1,1-difluoroethane, 1,1,1,2-tetrafluoroethane, dimethyl ether, and mixtures thereof. When reference is made to the total weight of the inventive compositions herein, such weight will be understood to exclude the weight of the propellant.

In one embodiment, a product is provided comprising an aerosol device including a container fitted with an dispenser, such as a dispensing valve, for dispensing the aerosol composition from the container. The container is charged with the composition according to the invention (e.g., comprising one or more particulate materials, one or more film formers, and volatile solvent). A suitable propellant may be included in the container with the inventive composition or may be included in a second container in a dual-chamber-type aerosol device. When the propellant is included in the container with the other ingredients, it will typically be present from about 20% to about 50%, by weight of the composition including propellant.

Particularly deleterious to the prevention and reduction of frizzy appearance in hair and the reduction of fly-away strands of hair are non-volatile water-soluble or water-dispersible components which may coat or mask the particulates on the surface of the hair, or which may attract or bind water, such as propylene glycol or glycerin. Preferably, the collective amount of such non-volatile water-soluble or water-dispersible components in the composition will be below about 15%, below about 10%, below about 5%, below about 2.5%, below about 1%, below about 0.5%, below about 0.25%, below about 0.1%, or below about 0.05%, based on the total weight of the composition. In some embodiments, the compositions are free of non-volatile water-soluble or water-dispersible components, and in particular, free of liquid water-soluble or water-dispersible components.

Other optional ingredients include, without limitation, silicone elastomers which may be incorporated to provide conditioning properties to the hair or improve the tactile properties of the film. Silicone elastomers are crosslinked flexible silicones that can undergo large reversible deformations. Such elastomers may be formed, for example, by platinum metal catalyzed reactions between SiH containing diorganopolysiloxanes and organopolysiloxanes having silicon bonded vinyl groups. Suitable silicone elastomers include dimethicone/vinyl dimethicone crosspolymers, vinyl dimethicone/methicone silsesquioxane crosspolymers, and dimethicone/phenyl vinyl dimethicone crosspolymers. Examples include Dow Corning 9040, 9041, and 9506, and Shin-Etsu KSG-15, 16, and 17, and Shin-Etsu KSP-100, 101, 102, 103, 104, 105, 200 and 300. The elastomers are preferably present at a concentration of 0.01% to 10%, more preferably at a concentration of 0.1% to 5%, and most preferably at a concentration of 1% to 3%. Silicone elastomers do not form good films, and are not included in the calculation of the powder to film former ratio. Vinyl dimethicone/Methicone/Silsesquioxane crosspolymer is one such silicone elastomer that has been found particularly useful. Other ingredients that can optionally be present include, without limitation, conditioners (e.g., Polyquaternium-37/PG Dicaprylate/Trideceth blend), aesthetic modifiers (e.g., Polymethyl Methacrylate spherical powder having a diameter of 4-8 µm), silicone resins (such as trimethylsiloxysilicate), thickeners (e.g., PEG-150/decyl alcohol/SMDI copolymer), sunscreens, preservatives, fragrances, etc.

Additional components may be incorporated as fillers or for various functional purposes as is customary in the cosmetic arts. However, while additional components consistent to formulate the above cosmetic compositions may be included, the inclusion of additional ingredients is limited to those ingredients which do not interference with the reduction or prevention of frizzy appearance of hair and the formation of a water vapor resistant film.

Anhydrous compositions of the invention may suitably be prepared by mixing the solvent (e.g., ethanol and cyclomethicone pentamer) with the particulate materials and the film former, and, if present, the shine enhancer and optional ingredients. There is essentially no restriction on the order of addition or manner of mixing these components. The composition may be mixed or homogenized at room temperature. It has been found useful but not necessary to mill the mixed ingredients which can be carried out using any suitable technique in the art. For example, a Silversen L4RT mixer operating at 4000 RPM for about 4 minutes has been found suitable. Once complete, the composition can be packaged, for example into a pump spray, or an aerosol spray which is then charged with propellant. In certain embodiments where the compositions are emulsions prepared from different phases, each prepared separately, the phases are combined and the emulsion may be formed by mixing or milling at room temperature, or by any other suitable means in the art.

The present invention provides a method for preventing or reducing frizzy appearance and fly away strands of hair comprising applying to a keratin fiber a hair care composition having a combination of a hydrophobic particulate material and a silicone-based hydrophobic film former, in particular, in dry, damaged, or curly hair. As used herein damaged hair any type of hair fibers that suffer from deleterious effects to appearance, feel or strength of the hair, including color treated hair as the dying process frequently results in damage to feel and strength of the hair fibers. However, the invention is not limited to application dry, damaged, or curly hair. The methods and compositions may be applied to any hair, including fine hair, to reduce or prevent frizzy appearance and impart a water-resistant film on the keratin fiber.

The inventive composition may be applied onto dry hair or wet hair. The compositions according to the invention are preferably applied to the hair (hair of the scalp, beard, mustache, etc.) to provide resistance against frizzy appearance. More preferably, the inventive composition may be distributed across strands of the hair forming a substantially uniform coating on the shafts of the hair fibers. The substantially uniform distribution may be achieved by spraying the composition across the hair and depositing the composition throughout the hair. The substantially uniform distribution may also be attained by applying the composition to the hair by hand and rubbing and spreading with fingers the composition across the hair. The composition may also be distributed in a substantially uniform manner throughout the hair using a brush or a comb. The composition may be applied to the hair and allowed to remain on the hair. Alternatively, hair treated with the composition may be rinsed with water after application of the composition to the hair. The composition can be re-applied at any time, as the consumer desires. In one embodiment, the composition may be applied daily, every other day, weekly or bi-weekly.

It has been found that the inventive compositions, when applied to the hair, particularly the hair of the scalp, may reduce and/or prevent fizzy appearance of hair, reduce unwanted volume, improve consumer's ability to control and maintain hair style (e.g., leaving hair more manageable or easier to style), reduce the amount of fly-away strands of hair, improve consumer's ability to obtain well-aligned hair (e.g., tames and smoothes unruly, frizzy, or flyaway hair), impart a desirable feel (e.g., soft or smooth) to hair, or improve consumer's ability to retain or extend the hairstyle, or change the volume of hair when applied to the hair, particularly the hair of the scalp. Particularly, the present invention imparts these properties to hair and protects from aesthetically undesirable changes to the hair particularly in humid conditions.

Volume of hair refers to the structural body and space occupied in defined regions of hair tresses and relates to the apparent thickness of hair by sight and touch, which also relates to the body of the hair. Body can be defined by feel, weight and hair set. Lack of body results in hair feeling limp, having less manageability. In some embodiments, the inventive compositions may reduce the volume of hair. For example, the inventive compositions may reduce the volume of hair by at least about 50%, at least about 60%, at least about 70%, at least about 75%, at least about 80%, at least 90%, or even at least about 100%. In other embodiments, the inventive compositions reduce the volume of hair by about 50% to about 100%, about 65% to about 95%, about 70% to about 90%, or about 75% to about 85%.

The benefits of the present invention may be imparted to the hair immediately after application of the compositions to the hair and may endure for a period of time following application of the compositions to the hair. The benefits may endure for a period of at least 6 hours, at least 8 hours, at least 12 hours or at least 18 hours. Preferably, the benefits may endure for an extended period of time. For example, in some embodiments, the benefits endure for at least 24 hours, at least 48 hours, at least 3 days, at least 5 days, or at least 1 week. In other embodiments, the benefits endure semi-permanently, by which is meant that the benefits endure for more than 1 week. In a preferred embodiment, hair treated with the inventive combination may retain some or all of the benefits identified above, particularly resistance to frizzy appearance, after at least one shampooing of the hair, by which is meant a single cycle of wetting, applying shampoo thereto, and rinsing of hair. In a more preferred embodiment, hair treated with the inventive combination may retain some or all of the benefits identified above, particularly resistance to frizzy appearance, after at least two, three, or more shampooings of the hair.

The foregoing may be tested using hair swatches treated with the inventive compositions. Likewise, the compositions may be applied to the hair of a pet, such as a dog, or fur materials, such as a fur coat, to improve the aesthetics of the hair.

Changes in volume of the hair may be determined on hair tresses using various techniques, including the technique described by C. R. Robbins and R. J. Crawford in the article "A Method to Evaluate Hair Body," J. *Soc. Cosmet. Chem.*, 35, pp. 369-377 (1984), the disclosure of which is hereby incorporated by reference herein, and modified versions thereof. Other suitable means for evaluating change in volume of hair involves taking a digital photograph of hair tresses and analyzing the photographs using an image analysis program, which is a commercially available testing service known as the Image Analysis Method from MarTech Personal Care. Another suitable means for evaluating change in volume of hair involves pulling a tress of hair through rings of different radial dimensions and relating the force required for pulling to a measure of volume or body. An exemplary method of this alternative test is performed using a Dia-Stron Miniaure Tensil Tester 175 and available as a commercially available testing service known as the Radial Compression/Ring Method from MarTech Personal Care. Preferably, the change in volume of hair may be examined using the testing protocol described below.

HAIR VOLUME TEST METHOD

The method consists of preparing fine virgin European brown hair in the form of swatches suitable to attach to a hair holder and a 2 cm ring. Each hair swatch is configured to appropriate weight and length for ring attachment and may be pre-treated by washing the tresses 2 to 3 times. Each of the washed virgin hair swatch is combed 5 times with a large end control comb prior to obtaining any measurements.

To test the volume of a hair tress, the hair swatch is pulled through the 2 cm ring at a constant rate. The forces applied to the tresses while the hair swatch is pulled through the 2 cm ring is measured using a Dia-Stron Miniature Tensil Tester 170. The amount of work for pulling each of the hair swatches through the ring is obtained by calculating the area under a curve of the measured forces applied to the hair tress over the length of the hair tress. All such measurements are obtained from dried hair.

Five to six measurement runs (curves) are taken of the washed virgin hair tresses before analysis. A baseline value is determined using the mean amount of work calculated from the measurements taken from the virgin tresses. The same hair tresses may then treated with a composition of the present invention. The treated hair tresses are allowed to dried and subsequently tested in the same manner. The percentage increase in volume is determined by comparing the mean amount of work measured from the treated hair tresses to the baseline mean work values obtained from the virgin tresses. An increase in work is indicative of an increase in hair volume.

EXAMPLES

Example 1

This Example provides compositions for preventing or reducing frizzy appearance of hair. Formulations 1A and 1B were prepared according to Table 1.

TABLE 1

| INCI name/description | 1A | 1B |
|---|---|---|
| Fumed Alumina (Aeroxide Alu C 805 fumed Alumina from Evonik Industries) | 1.00 | 1.25 |
| Dimethicone gum/Cyclopentasiloxane 15/85 (SF1214 from KOBO/Momentive) | 2.50 | 2-40 |
| Amodimethicone (SF 1708 from KOBO/Momentive) | 2.00 | 2.66 |
| Perfluorononyl Dimethicone | 1.00 | — |
| Dimethicone/Dimethiconol 87/13 (1403 Fluid from Dow Corning) | — | 0.24 |
| Polyquaternium-37/PG Dicaprylate/Trideceth blend | — | 0..25. |
| PEG-150/decyl alcohol/SMDI copolymer | — | 0.15 |
| Acrylates/Dimethicone copolymer/Methyl Trimethicone 40/60 (KP-549 from Shin-Etsu) | — | 3.00 |
| Alcohol SD 40B anhydrous | 22.00 | 9.70 |
| Water | — | 25.29 |
| Methyl Methacrylate crosspolymer (3d tech PW from KOBO) | 0.10 | 0.10 |
| Polymethyl Methacrylate spherical powder having a diameter of 4-8 μm (Ganzpearl GM-0600 from Presperse, Inc.) | 0.10 | 0.10 |
| Vinyl dimethicone/Methicone/Silsesquioxane crosspolymer (KSP-105 from Shin-Etsu) | 1.00 | 1.25 |
| Octylmethoxy Cinnamate | 0.80 | 0.53 |
| Fragrance | as needed | 0.80 |
| Preservatives | as needed | 0.80 |
| Cyclopentasiloxane (245 fluid from Dow Corning) | 69.50 | q.s. |
| TOTAL | 100.00 | 100.00 |

Formulation 1A is an exemplary embodiment of an anhydrous formulation. Formulation 1B provides an exemplary embodiment of a shake-well type emulsion. Emulsifiers may be added to Formulation 1B to provide a longer lasting emulsion or stable emulsion. Suitable emulsifiers including ethoxylated silicone emulsifiers, for example, PEG-10 dimethicone, PEG/PPG-18/18 dimethicone, PEG/PPG-19/19 dimethicone, cetyl PEG/PPG-10/1 dimethicone, amongst others.

The invention described and claimed herein is not to be limited in scope by the specific embodiments herein disclosed since these embodiments are intended as illustrations of several aspects of the invention. Any equivalent embodiments are intended to be within the scope of this invention. Indeed, various modifications of the invention in addition to those shown and described therein will become apparent to those skilled in the art from the foregoing description. Such modifications are also intended to fall within the scope of the appended claims. All publications cited herein are incorporated by reference in their entirety.

What is claimed:

1. A method for preventing or reducing frizzy appearance of hair comprising applying to the hair a composition comprising:
   (a) a hydrophobic particulate material having a median particle size between about 10 nm and about 20 μm comprising a hydrophobically surface-modified aluminum oxide, said hydrophobic particulate material comprising from about 0.1% to about 2.0% by weight of said composition;
   (b) a silicone-based hydrophobic film former comprising from about 0.5% to about 20% by weight of said composition; and
   (c) a volatile hydrocarbon or silicone fluid having a vapor pressure above about 0.01 mmHg at 20° C.;
   wherein the aggregate weight percentage of all non-volatile water-soluble or water-dispersible organic constituents in said composition is less than 5%, based on the entire weight of the composition.

2. The method according to claim 1, wherein said aluminum oxide is surface modified with alkylsilane groups.

3. The method according to claim 2, wherein said alkylsilane is caprylylsilane.

4. The method according to claim 3, wherein said aluminum oxide is fumed alumina.

5. The method according to claim 1, wherein said aluminum oxide is fumed aluminum oxide that is surface modified with alkylsilane groups.

6. The method according to claim 1, wherein said silicone-based hydrophobic film former comprises dimethicone, amodimethicone, dimethiconol, silicone polyurethane, silicone acrylate, or a combination thereof.

7. The method according to claim 6, wherein said silicone-based hydrophobic film former comprises a silicone acrylate copolymer.

8. The method according to claim 7, wherein said silicone acrylate copolymer is a copolymer comprising a poly(alkyl) acrylate backbone and a dimethicone polymer grafted to an alkyl ester side chain.

9. The method according to claim 1, wherein said composition is in the form of a liquid or emulsion.

10. The method according to claim 9, wherein the composition applied to the hair further comprises ethyl alcohol.

11. The method according to claim 9, wherein the composition applied to the hair is an emulsion further comprising water.

* * * * *